United States Patent [19]

Randles et al.

[11] Patent Number: 5,468,903
[45] Date of Patent: Nov. 21, 1995

[54] REGIOSELECTIVE SULFONYLATION REACTION OF SUBSTITUTED AROMATIC COMPOUNDS

[75] Inventors: Kenneth R. Randles; Brian G. Gott; Stephen T. A. K. Daley, all of Huddersfield, England

[73] Assignee: Zeneca Limited, London, United Kingdom

[21] Appl. No.: 22,709

[22] Filed: Mar. 1, 1993

[30] Foreign Application Priority Data

Mar. 3, 1992 [GB] United Kingdom ............. 9204529

[51] Int. Cl.$^6$ ............................................. C07C 315/00
[52] U.S. Cl. ............................. 568/28; 568/33; 568/35
[58] Field of Search ..................... 558/61, 53; 568/28, 568/34

[56] References Cited

U.S. PATENT DOCUMENTS 2,781,402  2/1957  Chadwick ........................... 568/34

FOREIGN PATENT DOCUMENTS 455332   3/1991   European Pat. Off. .
897735   5/1962   United Kingdom .
1010491  11/1965  United Kingdom .
2000134  1/1979   United Kingdom .

OTHER PUBLICATIONS

Hyatt et al., "Synthesis of Aryl Alkyl and Aryl Vinyl Sulfones via Friedel–Crafts Reactions of Sulfonyl Fluorides", Synthesis, No. 3, Mar. 1984, pp. 214–217.

*Primary Examiner*—José G. Dees
*Assistant Examiner*—Dwayne C. Jones
*Attorney, Agent, or Firm*—Marian T. Thomson

[57] ABSTRACT

A process for preparing a compound comprising a monocyclic aromatic ring having at least a first substituent and a substituted sulphonyl group at the position para to the first substituent, the process comprising mixing a reactant comprising the monocyclic aromatic ring with the first substituent and hydrogen in the position of the ring para to the first substituent, with a sulphonic acid halide derivative in the presence of a naturally occurring or synthetic zeolite capable of catalyzing a sulphonylation reaction between the reactant and the sulphonic acid halide, under conditions in which the reaction will occur.

14 Claims, No Drawings

REGIOSELECTIVE SULFONYLATION REACTION OF SUBSTITUTED AROMATIC COMPOUNDS

FIELD OF THE INVENTION

The present invention relates to a regiospecific sulphonylation reaction of substituted aromatic compounds.

BACKGROUND OF THE INVENTION

Sulphonylated aromatic compounds are useful intermediates in a wide range of fields such as in agrochemicals and polymers (see for example U.S. Pat. No. 4,780,127). European Patent Application No. 455332 describes certain reactions of aromatic compounds in the presence of zeolite catalysts.

The normal reaction between an aromatic compound and alkyl sulphonyl halide in the presence of an aluminum trichloride catalyst gives approximately 50% para selectivity. The applicants have provided a process whereby the para selectivity of such a reaction is enhanced.

SUMMARY OF THE INVENTION

According to the present invention there is provided a process for preparing a compound comprising a monocylic aromatic ring having at least a first substituent and a substituted sulphonyl group at the position para to said first substituent, the process comprising mixing a reactant comprising the monocyclic aromatic ring with said first substituent and hydrogen in the position of the ring para to said first substituent with, a sulphonic acid halide derivative in the presence of a naturally occurring or synthetic zeolite capable of catalyzing a sulphonylation reaction between said reactant and said sulphonic acid halide under conditions in which said reaction will occur.

DETAILED DESCRIPTION OF THE INVENTION

The monocyclic aromatic ring may be carbocyclic or heterocyclic. Examples of such rings include phenyl, or pyridyl or pyridinium, preferably phenyl.

The said first substituent may be any organic group provided only that it is not of sufficient size to preclude reaction in a zeolite catalyst. Suitably it is an electron-donating group so as to activate the para-hydrogen to electrophillic displacement. Examples of such substituents include alkyl, alkenyl, alkynyl, haloalkyl or alkoxy. Suitably the alkyl, alkenyl, alkynyl or haloalkyl group have up to twenty carbon atoms, but preferably up to 4 carbon atoms. Specific examples of such substituents are $C_{1-4}$ alkyl in particular methyl, iso-propyl or methoxy.

Other substituents may be present on the aromatic compound at the positions ortho and meta to the first embodiment are required. These substituents may include for example halo or hydroxy.

As used herein the terms "alkyl", "alkenyl" and "alkynyl" refer to straight or branched chains having for example up to 20 carbon atoms. The term "haloalkyl" refers to an alkyl group substituted by at least one halogen. The term 'aryl' includes phenyl and the term "halo" includes fluorine, chlorine, bromine and iodine.

Suitable sulphonic acid halide derivatives for use in the reaction are optionally substituted alkyl, optionally substituted alkenyl, optionally substituted alkynyl or optionally substituted aryl sulphonic acid halides. Suitable optional substituents for the alkyl, alkenyl, alkynyl and aryl groups include halogens such as fluorine and chlorine. In particular, the sulphonic acid halide derivative is a $C_{1-4}$ alkyl or halo $C_{1-4}$ alkyl sulphonic acid halide such as methane sulphonic acid halide, ethane sulphonic acid halide or trifluoromethylsulphonic acid halide.

Preferred sulphonic acid halides are sulphonic acid chlorides or fluorides in particular chlorides.

Suitable reaction conditions are temperatures for example of 20° C. to 250° C., such as from 110° C. to 250° C., usually at the reflux temperature of the reactant, or if required, of an inert organic solvent in which the reaction is affected. The reaction may be continued for extended periods of from 1 to 72 hours until a reasonable yield of desired product is achieved. This will generally be dependent upon the nature of the reactants and the particular zeolite catalyst employed.

In particular the present invention provides a process for preparing a compound of formula (I), where $R^1$ is optionally substituted alkyl or phenyl, $R^2$ is alkyl, alkenyl, alkynyl, haloalkyl or alkoxy and $R^3$ and $R^4$ are independently selected from hydrogen, halo or hydroxy; which process comprises reacting a compound of formula (II), where $R^2$, $R^3$ and $R^4$ are as defined in relation to formula (I) with compound of formula (III), where $R^1$ is as defined in relation to formula (I) and X is a halogen leaving group, in the presence of a naturally occurring or synthetic zeolite capable of catalyzing the reaction.

Preferably $R^1$ is a $C_{1-6}$ alkyl, groups such as methyl or ethyl, trifluoromethyl, or phenyl. Most preferably $R^1$ is methyl.

Preferably $R^2$ is an alkyl group such as $C_{1-6}$ alkyl in particular methyl, isopropyl or methoxy.

Suitably $R^3$ and $R^4$ are selected from hydrogen, fluoro, chloro or hydroxy. Preferably $R^3$ and $R^4$ are selected from hydrogen and fluoro.

Examples of compounds of formula (II) include toluene, cumene, ortho-fluoro toluene, meta-fluoro toluene, anisole and meta cresol.

Where such compounds of formula (II) are employed, the reaction may be affected without additional solvents being added. Alternatively organic solvents in which the reaction occurs may also be present. Suitable solvents may include nitrobenzene, benzonitrile, chlorinated hydrocarbons such as ethylene dichloride or trichloroethylene, di-isopropyl ketone, 4-methyl pentan-2-one tetrahydrofuran. Said solvents may be mixed with water.

A preferred organic solvent is nitrobenzene, which may be in the presence of water, in particular the nitrobenzene employed may contain from 4–40 mol% water.

Suitable leaving group X include chloro and fluoro.

The selection of a suitable zeolite can be determined by routine procedures well known to the skilled chemist. A particularly preferred class of zeolite for use in this reaction in zeolite ZSM5, X or Y type zeolites, or zeolite beta. A particularly preferred zeolite when applied in certain reactions is CP 811 type β zeolite sold under the trade name 'VALFOR'.

The zeolite may be in the form of a powder or granules or in the form of shaped particles, such as cylinders, or in the form of porous beads. In the reactions of the invention, the zeolite may be used in the form of a packed bed. As an alternative, a suspension of the zeolite in the reactor may be used. In the latter case amount of zeolite present should be sufficient to catalyze the reaction in a reasonable timescale.

This will depend upon many factors including the nature of the reactant and the particular zeolite used. In most cases, an amount of from 0.2–2.2 g of catalyst per gram of sulphonic acid halide present will generally be acceptable.

The zeolite may be associated with an inorganic matrix which is preferably inert. The matrix may be present solely as a binding agent to hold particles of the zeolite together, or it may function as an inert diluent. Suitable inorganic matrices and diluents include conventional support materials such as silica, clays such as bentonites, synthetic porous materials such as silica-zirconia and aluminas.

After use the zeolite catalyst may be recovered and recycled. Calcining prior to reuse will assist in maintaining the activity of the zeolite.

The invention will now be illustrated by references to the following Examples.

EXAMPLE 1

Toluene (0.94 mols) was added to a 250 ml round-bottom multi-neck flask and attached to this is a Dean-Stark arm, condenser and a calcium chloride guard tube. Zeolite was added as indicated in Table I and the preparation continually stirred using an over-head stirrer and refluxed for 3 hours until all the water in the zeolite was removed. After cooling, methane sulfonyl chloride (0.15 mols) was added slowly over five hours and refluxed (100° C.) from the first acid addition for periods as indicated in Table I. The crude reaction mixture was cooled and caustic (20gNaOH in 300 mls) water added. The organic phase was extracted with ethylacetate, dried with magnesium sulfate and any solvent is removed in the rotary evaporator.

The ratio of the ortho: meta: para methane sulphonyl toluene present in the product as determined by G.L.C. is shown in Table I.

TABLE I

| Zeolite | Product Ortho:meta:para | Reflux time/hr |
| --- | --- | --- |
| 10 g of Beta cp811b-25 | 0.16:0.06:1 | 24 |
| 10 g of Beta cp811b-25 | 0.12:0.06:1 | 48 |
| 10 g of Beta cp811b-25 | 0.08:0.04:1 | 72 |
| 5 g of Beta cp811b-25 | 0.02:0.10:1 | 24 |
| 5 g of Beta cp811b-25 | 0.09:0.03:1 | 48 |
| 5 g of Beta cp811b-75 | 0.09:0.04:1 | 24 |
| 5 g of Beta cp811b-75 | 0.07:0.04:1 | 48 |
| 5 g of Beta cp811b-75 | 0.08:0.04:1 | 72 |

The product of Example 1 can for instance be chlorinated (see U.S. Pat. No. 4,675,447) and then oxidized (see WO90/06302) to yield 2-chloro-4-methanesulphonylbenzoic acid, an intermediate useful in the preparation of herbicides (see for example WO90/06301).

EXAMPLE 2

Cumene (0.94 mols) was added to a 250 ml round-bottomed multi-neck flask and attached to this is a Dean-Stark arm, condenser and a calcium chloride guard tube. Zeolite Beta cp811 75 (5 g), was added and the preparation continually stirred using an over-head stirrer and refluxed for 3 hours until all the water in the zeolite was removed. After cooling, methane sulfonyl chloride (0.15 mols) was added slowly over five hours and refluxed (100° C.) from the first acid addition for 24 hours. The crude reaction mixture was cooled and caustic (20gNaOH in 300 mls) water added. The organic phase was extracted with ethylacetate, dried with magnesium sulfate and any solvent is removed in the rotary evaporator.

The ratio of the ortho: meta: para methane sulphonyl cumene present in the product was found by G.L.C. to be 0.013:0.07:1.

EXAMPLE 3

Anisole was dried to prior to use over 3A molecular sieves. Catalyst comprising Zeolite CP811B was activated in an oven at 180° C. for 3 to 4 hours. Anisole (0.10 mol) was charged to a nitrogen dried 250 ml reaction flask fitted with a water condenser, thermometer and a drying tube. Mesyl chloride (0.1 mol) was then charged to the flask followed by the activated catalyst. The contents of the flask were then agitated and heated under reflux for 18 hours.

After allowing the contents of the flask to cool, the liquid phase was separated from the catalyst by filtration. The catalyst was washed with dry acetone (100 ml).

Analysis of the liquid phase by GCMS was used to identify the products and isomer distribution.

The ratio of p-mesyl anisole: m-mesyl anisole: o-mesyl anisole in the product was 5.7: 2.3:1.

EXAMPLE 4

A range of aromatic substrates A and nitrobenzene were dried prior to use over 3A molecular sieves. Samples of catalyst comprising Zeolite CP811B were activated in an oven at 180° C. for 3 to 4 hours. The aromatic substrate A comprising (0.10 mol) was charged to a nitrogen dried 250 ml reaction flask fitted with a water condenser, thermometer and drying tube. A sulphonyl chloride B (0.10 mol) was then charged to the flask together with nitrobenzene (123 g). The activated catalyst (5 g of CP811B-75) was then charged. The contents of the flask were agitated and heated under reflux for 18 hours.

After allowing the reaction to cool, the liquid phase was separated from the catalyst by filtration. The catalyst was then washed with dry acetone (100 ml).

A mixture of products was obtained. Analysis of the liquid phases by GCMS was used to identify the products and in particular the isomer distribution of the sulphonylated aromatic products.

TABLE II

| Experiment | A | B | Yield p isomer | ratio p:m:o isomers |
| --- | --- | --- | --- | --- |
| 1 | Anisole | mesyl chloride | 0.7% | 1.75:1:1 |
| 2 | 2-fluorotoluene | ethane sulphonyl chloride | 2.0% | — |
| 3 | 3-fluoro | ethane sulphonyl chloride | 2.8% | — |
| 4 | 2-fluoro | mesyl chloride | 1.7% | — |
| 5 | toluene | p-tosyl chloride | 20% | — |

— means no meta or ortho isomers detected.

EXAMPLE 5

Toluene was dried prior to use over 3A molecular sieves. Catalyst was activated in an oven at 180° C. for 3 to 4 hours. Toluene (0.10 mol) was charged to a nitrogen dried 250 ml reaction flask fitted with a water condenser, thermometer and a drying tube. Methane sulphonyl chloride (0.1 mol)

was then charged to the flask followed by the activated catalyst (5.0 g of CP11B-75). The contents of the flask are then agitated and heated to reflux and held for 18 hours.

After allowing the contents of the flask to cool, the liquid phase was separated from the catalyst by filtration. The catalyst was washed with dry acetone (100 ml).

Analysis of the liquid phase by GCMS showed the presence of the para, ortho and meta isomers of mesyl toluene in the ratio 73:20:6 respectively. The yield of the para isomer based on mesyl chloride charged was 6.3%.

EXAMPLE 6

Toluene and nitrobenzene were dried prior to use over 3A molecular sieves. The catalyst was activated in an oven at 180° C. for 3 to 4 hours. Toluene (0.10mol) was charged to a nitrogen dried 250 ml reaction flask fitted with a water condenser, thermometer and drying tube. Methane sulphonyl chloride (0.10 mol) was then charged to the flask together with nitrobenzene (160.4 g). The activated catalyst (13.7 g of CP811B-75) was then added. The water content of the system is then adjusted to 0.23 g. The contents of the flask are agitated and heated at reflux for 18 hours.

After following the contents of the flask to cool, the liquid phase was separated from the catalyst by filtration. The catalyst was washed with dry acetone (100 ml).

Analysis of the liquid phases by GCMS showed the presence of the para, ortho and meta isomers of mesyl toluene in the ratio 81:12:7 respectively. The yield of the para isomer based on mesyl chloride charged was 30.8%.

EXAMPLE 7

Toluene and nitrobenzene were dried prior to use over 3A molecular sieves. The catalyst was activated in an oven at 180° C. for 3 to 4 hours. Toluene (0.10 mol) was charged to a nitrogen dried 250 ml reaction flask fitted with a water condenser, thermometer and drying tube. Methane sulphonyl chloride (0.10 mol) was then charged to the flask together with nitrobenzene (123 g). The activated catalyst (5 g of CP811B-75) was then charged. The contents of the flask were agitated and heated at reflux for 18 hours.

After allowing the reaction to cool, the liquid phase was separated from the catalyst by filtration. The catalyst was then washed with dry acetone (100 ml).

Analysis of the liquid phases by GCMS showed the presence of the para, ortho and meta isomers of mesyl toluene in the ratio 81:13:6 respectively. The yield of the para isomer based on mesyl chloride was 13.9%.

CHEMICAL FORMULAE
(in description)

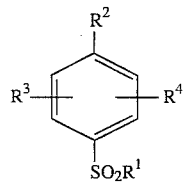

(I)

-continued
CHEMICAL FORMULAE
(in description)

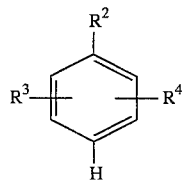

(II)

$R^1SO_2X$ (III)

We claim:

1. A process for preparing a compound comprising a monocyclic aromatic ring at least a first substituent and a substituted sulphonyl group at the position para to said first substituent, the process comprising mixing a reactant comprising the monocyclic aromatic ring with said first substituent and hydrogen in the position of the ring para to said first substituent, with a sulphonic acid halide derivative in the presence of a naturally occurring or synthetic zeolite capable of catalysing a sulphonylation reaction between said reactant and said sulphonic acid halide, under conditions in which said reaction will occur, wherein said sulphonic acid halide derivative is selected from optionally substituted alkyl, optionally substituted alkenyl and optionally substituted alkynyl sulphonic acid halides.

2. A process according to claim 1 wherein the said monocyclic aromatic ring is selected from phenyl, and pyridyl or pyridinium.

3. A process according to claim 2 wherein said monocyclic aromatic ring is phenyl.

4. A process according to claim 1 wherein said first substituent comprises an electron-donating group.

5. A process according to claim 4 wherein said electron-donating group is selected from methyl, iso-propyl and methoxy.

6. A process according to claim 1 where the reaction is effected in the presence of an organic solvent selected from nitrobenzene, benzonitrile, di-isopropyl ketone, 4-methyl pentan-2-one, tetrahydrofuran and halogenated hydrocarbon solvent any of which may be mixed with water.

7. A process according to claim 6 where the solvent is nitrobenzene.

8. A process according to claim 1 wherein from 0.2–2.2 g of catalyst per gram of sulphonic acid halide is used.

9. A process according to claim 1 wherein after the reaction is complete, the zeolite catalyst is recovered and calcined.

10. A process for preparing a compound of formula (I),

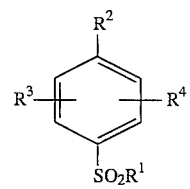

(I)

wherein $R^1$ is optionally substituted alkyl, $R^2$ is alkyl, alkenyl, alkynyl, haloalkyl or alkoxy and $R^3$ and $R^4$ are independently selected from hydrogen, halo and hydroxy; which process comprises reacting a compound of formula (II),

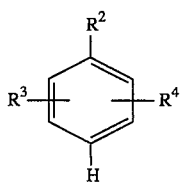

(II)

where $R^2$, $R^3$ and $R^4$ are as defined in relation to formula (I) with a compound of formula (III), $$R^1SO_2X \quad \quad (III)$$

where $R^1$ is as defined in relation to formula (I) and X is a halogen leaving group, in the presence of a naturally occurring or synthetic zeolite capable of catalyzing the reaction.

11. A process according to claim 10 wherein $R^1$ is methyl, ethyl or trifluoromethyl.

12. A process according to claim 10 where $R^2$ is a $C_{1-6}$ alkyl group.

13. A process according to claim 10 wherein the compound of formula (II) is toluene or cumene.

14. A process for preparing a compound comprising a monocyclic aromatic ring having at least a first substituent and a substituted sulfonyl group at the position para to said first substituent, the process comprising mixing a reactant comprising the monocyclic aromatic ring with said first substituent and hydrogen in the position of the ring para to said first substituent, with a ($C_1$–$C_4$) alkyl or halo ($C_1$–$C_4$) alkyl sulphonic acid halide in the presence of a naturally occurring or synthetic zeolite capable of catalyzing a sulfonylation reaction between said reactant and sulfonic acid halide, under conditions in which said reaction will occur.

* * * * *